United States Patent [19]

Baumgart et al.

[11] 4,170,990

[45] Oct. 16, 1979

[54] METHOD FOR IMPLANTING AND SUBSEQUENTLY REMOVING MECHANICAL CONNECTING ELEMENTS FROM LIVING TISSUE

[75] Inventors: Frank Baumgart, Ratingen, Fed. Rep. of Germany; Günter Bensmann, Essen; Jörg Haasters, Essen; Jürgen Hartwig, Essen; Joachim Jorde, Essen; Manfred Müller, Essen; Karl F. Schlegel, Essen, all of Fed. Rep. of Germany

[73] Assignee: Fried. Krupp Gesellschaft mit beschränkter Haftung, Essen, Fed. Rep. of Germany

[21] Appl. No.: 873,052

[22] Filed: Jan. 27, 1978

[30] Foreign Application Priority Data

Jan. 28, 1977 [DE] Fed. Rep. of Germany ....... 2703529

[51] Int. Cl.² .............................................. A61F 5/04
[52] U.S. Cl. ................................... 128/92 B; 128/69; 128/84 R; 128/92 BC; 128/92 D; 128/92 G
[58] Field of Search .................. 3/1.7; 128/84 R, 69, 128/92 D, 92 B, 92 BC, 92 G

[56] References Cited

U.S. PATENT DOCUMENTS

| 3,606,592 | 9/1971 | Madurski et al. ................. 3/1.7 X |
| 3,786,806 | 1/1974 | Johnson et al. ................. 128/92 D |
| 3,827,426 | 8/1974 | Page et al. ...................... 3/1.7 X |

*Primary Examiner*—Clifford D. Crowder
*Attorney, Agent, or Firm*—Spencer & Kaye

[57] ABSTRACT

Method for implanting and subsequently removing mechanical implants of an Ni-Ti or a Ti-Nb alloy material which exhibits the memory effect which occurs due to heating of the implant to a temperature above the specific temperature for the alloy material. The memory effect is actuated by heating the implant after implantation of same in the living tissue, and upon completion of the healing process, the implant is substantially returned to its shape upon implantation by cooling it to a temperature below the temperature which actuates the opposite memory effect to facilitate removal.

3 Claims, 21 Drawing Figures

FIG.1a   FIG.1b
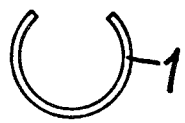 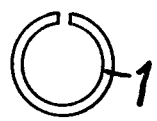
FIG.1c   FIG.1d   FIG.1e
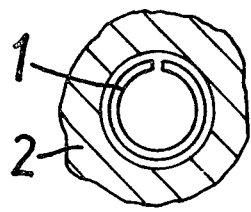 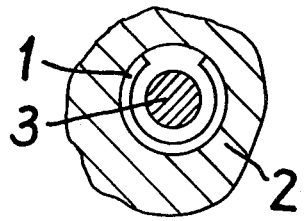 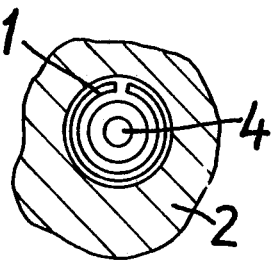
FIG.2a   FIG.2b   FIG.2c   FIG.2d
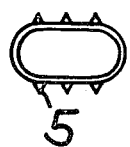   
FIG.3a   FIG.3b   FIG.3c   FIG.3d
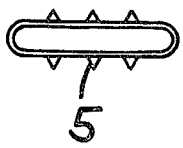 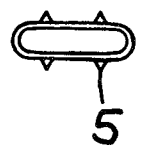 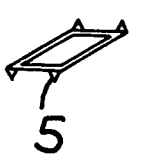 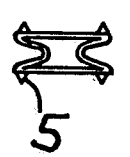

METHOD FOR IMPLANTING AND SUBSEQUENTLY REMOVING MECHANICAL CONNECTING ELEMENTS FROM LIVING TISSUE

BACKGROUND OF THE INVENTION

The present invention relates to the implantation into living tissue of mechanical implants made of an Ni-Ti alloy or a Ti-Nb alloy while utilizing the memory effect due to heating of the implants to a temperature above the temperature specific for the particular material.

It is known in medicine to use unchangeably rigid implants—such as, for example, nails, clamps and pins—with which tissue separations or breaks are connected together mechanically. In such cases, the separated or broken pieces of tissues, e.g. bones, are pressed against one another by means of external clamping devices and screwed plates, so that a pressure develops which enhances healing. Also known are prosthetic parts which serve as bond substitutes and which must either be cemented in place or must be screwed to the bone.

The art also knows materials under the name "memory alloys" (see, for example, German Auslegeschrift (Published Patent Application) No. 2,661,710 which, once they have been appropriately preshaped, are capable of performing mechanical work during a later heat treatment. This behavior of these alloy materials, which is based on a change in their structure, resides in that certain alloys, after plastic deformation will return to their original shape, i.e., the shape before the deformation after having been heated to above a certain temperature which is specific for the particular material involved. The temperature range in which a structure modification produced by a plastic deformation is spontaneously reversed is called the conversion temperature range. For an alloy consisting of 55 weight percent Ni and 45 weight percent Ti, this conversion range lies, for example, at about 60° C. A change in the percentage composition or the addition of Fe, Co, Mn, Al, Au or zirconium produces a shift in the conversion temperature. Thus it is possible to actuate thermally controlled forces by suitable selection of the composition of a "memory alloy".

U.S. Pat. No. 3,786,806, issued Jan. 22nd, 1974, proposes to use plates of a memory alloy for surgical purposes. According to this patent, the plates of memory alloy are initially prestretched, are then fastened to the fractured bone pieces by means of screws and are then heated. Due to changes in their structure, the plates become shorter and if necessary, produce the pressure required to heal the fracture at that point. Upon completion of the healing process, the screws or similar fastening elements must be removed from the bone. There then exists the danger that the just healed bones receive tissue damage.

SUMMARY OF THE INVENTION

It is the object of the present invention to overcome the drawback in the prior art methods of using implants of memory alloys.

The above object is achieved according to the present invention by a method of implanting and subsequently removing mechanical connecting elements from living tissue, wherein: a connecting element is provided which is formed of a Ni-Ti of a Ti-Nb alloy material that exhibits a memory effect due to heating to a temperature above a material specific temperature and which has been plastically deformed; the connecting element is implanted and thereafter heated to a temperature sufficient to actuate the memory effect to cause the element to assume substantially its shape prior to being plastically deformed and to provide the desired connection between portions of living tissue; upon completion of the healing process for the living tissue, the implanted connecting element is cooled to a temperature below that which actuates the opposite memory effect to return the implanted connecting element to substantially its shape upon implantation; and then the connecting element is removed.

This method is advantageously not only gentle to tissues but also, compared to the previously required surgical efforts for implants, surprisingly easy to accomplish. Practically any prior art connecting element, such as, for example, nails, wires, sutures, clamps, clips, sleeves, rings, discs, pins or tubes, can serve as a possible implant made of a memory alloy. Separations in living tissue can be fixed, depending on the plastic deformation involved, by rotating, compressing, bending or twisting of the implant by utilization of the memory effect. Advantageously, the removal of the implant from the living tissue is just as devoid of problems as its insertion.

If the separated tissue parts are to be fixed in stages or the implants are to be removed in stages after a partially completed healing process, it is possible to apply heat or cooling in stages so that the final state of the implant is attained in several stages. This can also be accomplished in that the implants are made of a plurality of alloys containing different percentages of elements in their composition. Each one of these memory alloys has a certain conversion temperature range, so that it is possible to actuate the "memory effect" several times using different controlled temperatures for the several alloys. Due to the functional dependency of the conversion temperature on the percentage composition of the "memory alloy", the effect can be initiated between body temperature and much higher temperatures.

BRIEF DESCRIPTION OF THE DRAWINGS

FIGS. 1a through 1e show the individual steps of the method according to the invention for implanting as well as for removing a marrow nail.

FIGS. 2a–2d show distraction pieces, which can be used as implants in the method according to the invention, in the state after actuation of the one time memory effect.

FIGS. 3a–3d show the distraction pieces according to FIGS. 2a–2d respectively in their configuration prior to actuation of the one time memory effect.

FIG. 5b is a top view of the disc clamp according to FIG. 5a.

FIG. 5c is a cross-sectional view along the line A—A of FIG. 5a.

FIG. 5d is a cross-sectional view along the line B—B of FIG. 5a.

DETAILED DESCRIPTION OF THE PREFERRED EMBODIMENTS

Figure 4A:
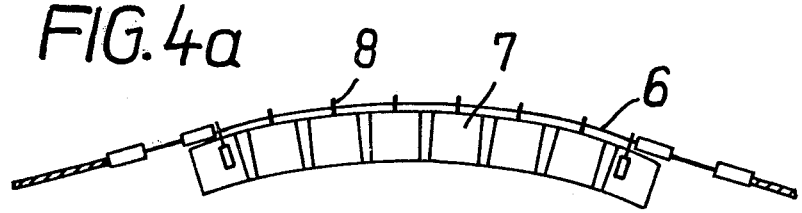
FIGS. 4a through 4d show the individual method steps for a scoliosis operation by means of wires of memory alloys.

The following method is employed according to the invention for the use of implants made of "memory alloys". After installation of the implant which has been previously plastically deformed to a desired shape, the implant is heated from room temperature to body temperature. An additional input of heat actuates the one-time "memory effect". The final temperature at which the conversion to an austenitic structure of the implant is to be completed should not be any higher than 60° in order to avoid damage to the surrounding tissue. Once the implant has taken on its final shape as a result of structural conversions, the additional heat is removed and the implant is cooled to body temperature. To remove such an implant from the body, this process can be assisted in that the temperature of the implant is reduced, via a cooling device comprising, for example, a probe through which a coolant flows, to below the temperature at which the formation of martensitic structures in the implant is completed. This produces the so-called repeatable memory effect which constitutes a reversal of the original direction of movement of the implant. If it is impossible to employ memory alloys which are compatible with the surrounding living tissue, the implants may be encased in a tissue compatible protective coating. In a particularly advantageous embodiment, this coating contains heat insulating materials.

The implants inserted into a body may have various geometric shapes. One field of application is the use of marrow nails, which is shown in FIGS. 1a–1e. With marrow nails of the conventional design, the problem of the formation of a fat embolism exists since the marrow nails are hammered into a predrilled marrow channel of smaller dimension. On the other hand, there often exist great difficulties in removing the nail after healing since overcoming the adhesion in the marrow channel requires great pulling forces which must be exerted on the end of the nail and often result in breaks in the surrounding bone. The proposed marrow nail comprises a tube of memory alloy which has been slit along its longitudinal axis and which may for example, have a circular, elliptical, clover-leaf or other rotation preventing cross section, which may also be variable along the axis of the nail. FIG. 1a shows a marrow nail in the shape of a slit tube of a memory alloy which has a circular cross section. The tube of FIG. 1a is plastically deformed to provide the prepared marrow nail having a reduced diameter as shown in FIG. 1b and the prepared marrow nail is loosely inserted into the slightly, or not at all, predrilled marrow channel of a bone 2 which has been broken or fractured, as shown in FIG. 1c. By means of a heating probe 3 the marrow nail 1 is heated and thus expands as shown in FIG. 1d. This achieves a relative fixing of the two bone ends along the marrow channel axis. Compression of the fracture is effected by the available muscle tension. If it should be necessary, the marrow nail 1 may also be additionally prestretched along its longitudinal axis so that it is additionally compressed in the longitudinal direction when heated. In this case it is necessary, however, to anchor the nail 1 at both of its ends which anchoring can be effected, for example, by sprockets or teeth on the outer surface of the nail. In this case the memory effect is actuated by localized heating, first at the two ends and then in the center region of the nail. To remove the nail 1, as shown in FIG. 1e, a cooling probe 4, through which, for example, a coolant flows or which is merely filled with a frozen medium of high specific heat, is inserted into the marrow channel. The cooling effect reduces the temperature of the marrow nail 1 to the martensitic temperature to actuate the reverse memory effect and redeformation leads to the nail coming loose from the wall of the marrow channel so that the nail can be removed with ease.

FIGS. 2a–2d and 3a–3d show possible configurations for distraction pieces in their heat-treated and plastically deformed configurations respectively. When forming artificial bone bridges in regions which are accessible only with great difficulty, e.g., in order to stiffen joints or other bone members which normally are movable relative to one another, it is desirable to avoid such relative movement during the period of formation of stressable bone substance from implanted bone chips, and to relatively arrest the adjacent bone edges. This increases the chances of healing and shortens the patent's total period of immobility. Spacer or pressure elements of memory alloys can here be used to advantage. These elements may have various shapes but should, if possible, be thin-walled hollow bodies so that easy and rapid heating or cooling by means of a probe inserted into their interiors can be assured. In order to prevent relative shifts and to improve anchoring, humps 5, e.g., teeth, tongues or the like, may be applied on the exterior of such hollow bodies. Such distraction pieces could have the shapes, for example as shown in FIGS. 2a–2d and 3a–3d and can be inserted and removed in the same manner as the above-mentioned marrow nail.

The following example describes a specific application of a marrow nail:

The marrow nail used, consisting of a 55.3 % b.wt. Ni alloy with the balance titanium, had a length of 400 mm and a diameter of 15 mm. The bone canal was pre-bored to a diameter of 16 mm and permitted easy insertion of the marrow nail. Following insertion, the nail was heated to 45° C. within 10 seconds by means of water of 60° C. passed through its hollow interior at a rate of 5 l/min. As a result of martenistic transformation, the nail expanded and pressed itself against the pre-bored bone walls. After complete healing, the nail was cooled with water of 5° C. at the same flow rate of 5 l/min. for a period of 20 seconds. This cooling caused the marrow nail to contract to its original diameter of 15 mm. The heat required in each case for initiating the "memory-effect" is calculated on the basis of the material's specific heat capacity of 0.32 J/gK and its heat of transformation which amounts to 24.2 J/g for the nail used here.

Figure 4B:
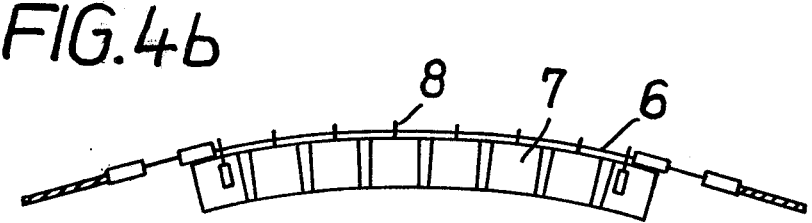
Figure 4C:
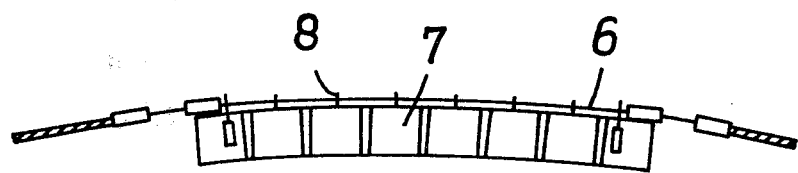
Figure 4D:
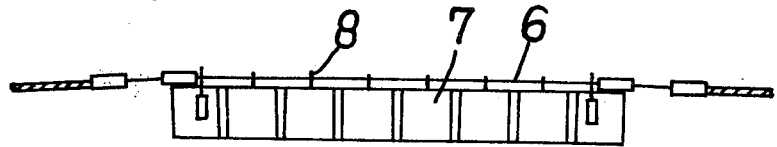
Figure 5A:
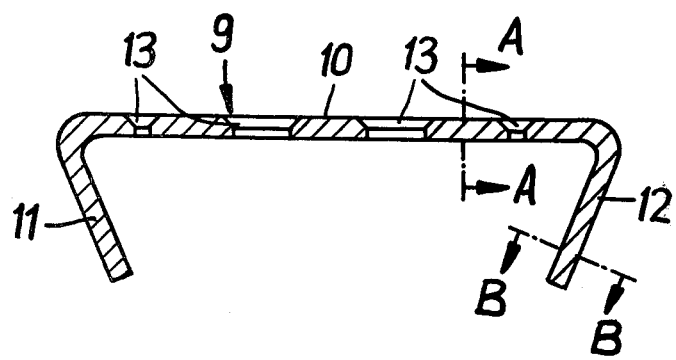
FIG. 5a is a longitudinal sectional view of a disc clamp formed of a memory alloy.
Figure 5B:
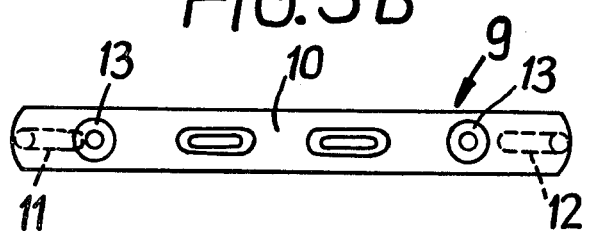
Figure 5C:
Figure 5D:

FIGS. 4a–4d show the use of a wire of a memory alloy for alignment and connecting purposes. The method with which a curved spine as a result of scoliosis is straightened by means of an attached memory wire 6 will be demonstrated at a model. Heating to actuate the memory effect is effected directly via the electric resistance of the memory wire 6. The wire is pre-stretched and, as shown in FIG. 4a, is clamped by appropriate means without tension, to both ends of the model which represents vertebrae 7. The wire 6 is passed through eyes 8, which are connected to the respective vertebrae, and becomes shorter due to heating, as shown in FIGS. 4b through 4d so that, as shown in FIG. 4d, the spine is straightened. Even thin wires, which in so-called wire rings are used to connect bone sections, can be pulled together by heating after they have been anchored by means of clamps or knots.

The wire used in the example illustrated in FIGS. 4a–4d consisted of 55.3 percent b.wt. Ni with balance titanium and had a diameter of 3 mm. After healing of the vertebrae in the corrected position, the wire was cooled down to 5° C., the resulting martenistic transformation having the effect of expanding it to its pre-implantation length and hence making it easy to remove.

FIG. 5 shows a disc clamp of a particular type. For conventional osteosynthesis, gaping open of the fracture on the side facing away from the applied plate or connecting element is prevented by prebending the plate before its insertion or implantation. In principle, such prebending is also possible with plates formed of a memory alloy. It is then necessary to initially produce a curved configuration and to imprint this on the plate as its virgin shape. Then the plate is bent straight again and is stretched by the predetermined amount. This process has the drawback that different degrees of expansion are present at the edge grains of the plate facing the bone and away from the bone. Such preheated plates may initially warp if with uniform heating the memory effect starts earlier in the grains away from the bone than in the grains facing the bone. The "plate clamp" 9 shown in FIG. 5 in its virgin state, i.e., prior to plastic deformation, circumvents these difficulties. The clamp 9 has a center portion 10 with the cross-sectional shape of the known osteosynthesis plates of memory material as shown in FIG. 5c, but then tapers at its two ends or legs 11 and 12 to a circular rod shape as shown in FIG. 5d. Then the two legs 11 and 12 are bent open so that each leg forms a right angle with the center portion 10 and the center portion 10 of the clamp is stretched. After straightening of the broken bone, the holes are made for the implant legs 11 and 12 and the clamp 9 is additionally fixed, if necessary, by two screws via openings 13. Then the memory effect to return the clamp 9 to the shape shown in FIG. 5a can be actuated by the introduction of heat. While the contraction of the center portion 10 presses the fracture together, and produces a healing-enhancing pressure in the fracture gap, bending back of the clamp legs 11 and 12 prevents gaping of the fracture on the side away from the plate 9.

The alloy employed in the example illustrated in FIGS. 5a–5d consisted of 55.3 % b.wt. Ni with the balance titanium. The bone plate was implanted and, with a heat supply of 0.32 J/gK, heated to a temperature of 50° C. and transformed to its condition prior to preforming by a heat of transformation of 24.2 J/g. After complete healing, the plate was cooled down to 10° C. so that it assumed its pre-implantation state in which it could be easily removed.

It will be understood that the above description of the present invention is susceptible to various modifications, changes and adaptations, and the same are intended to be comprehended within the meaning and range of equivalents of the appended claims.

What is claimed is:

1. A method of implanting and subsequently removing mechanical connecting elements from living tissue comprising: providing a connecting element which is formed from the group consisting of a Ni-Ti or a Ti-Nb alloy material which exhibits a memory effect due to heating to a temperature above a material specific temperature and which has been plastically deformed; implanting the connecting element; thereafter heating the connecting element to a temperature sufficient to actuate the memory effect to cause the element to assume substantially its shape prior to being plastically deformed and to provide the desired connection between portions of living tissue; upon completion of the healing process for the living tissue, cooling the implanted connecting element to a temperature below that which actuates the opposite memory effect to return the implanted connecting element to substantially its shape upon implantation; and then removing the connecting element.

2. A method as defined in claim 1 wherein said step of cooling includes cooling to a temperature below that at which the formation of martinsitic structures of said alloy material is completed.

3. A method as defined in claim 1 wherein said connecting elements are thin walled hollow bodies; wherein said step of heating includes placing a heating probe in the interior of the hollow body; and wherein said step of cooling includes placing a cooling probe in the interior of the hollow body.

* * * * *